(12) United States Patent
Cui et al.

(10) Patent No.: US 12,005,128 B1
(45) Date of Patent: Jun. 11, 2024

(54) NEAR INFRARED SMALL MOLECULE PROBES FOR THE DETECTION OF CELLULAR SENESCENCE

(71) Applicants: Lina Cui, Gainesville, FL (US); Jun Liu, Gainesville, FL (US); Xiaowei Ma, Gainesville, FL (US); Ying Wang, Albuquerque, NM (US); Philip Deenik, Albuquerque, NM (US)

(72) Inventors: Lina Cui, Gainesville, FL (US); Jun Liu, Gainesville, FL (US); Xiaowei Ma, Gainesville, FL (US); Ying Wang, Albuquerque, NM (US); Philip Deenik, Albuquerque, NM (US)

(73) Assignee: UNM Rainforest Innovations, Albuquerque, NM (US)

( * ) Notice: Subject to any disclaimer, the term of this patent is extended or adjusted under 35 U.S.C. 154(b) by 644 days.

(21) Appl. No.: 16/838,907

(22) Filed: Apr. 2, 2020

Related U.S. Application Data

(60) Provisional application No. 62/828,242, filed on Apr. 2, 2019.

(51) Int. Cl.
*A61K 49/00* (2006.01)
*G01N 33/58* (2006.01)
*C07D 491/052* (2006.01)

(52) U.S. Cl.
CPC ...... *A61K 49/0043* (2013.01); *A61K 49/0058* (2013.01); *G01N 33/582* (2013.01); *C07D 491/052* (2013.01); *G01N 2458/00* (2013.01)

(58) Field of Classification Search
CPC .......... A61K 49/0043; A61K 49/0058; G01N 33/582; G01N 2458/00; C07D 491/052
USPC .......................................... 424/9.6
See application file for complete search history.

(56) References Cited

U.S. PATENT DOCUMENTS

2014/0010763 A1* 1/2014 Shabat ................ C07D 213/30
546/264

OTHER PUBLICATIONS

Kwan et al. Angew Chem. Int. Ed. 2011, 50, 300-303. (Year: 2011).*
Zhang et al. Analyltica Chimica Acta 986m (2017) 97-104. (Year: 2017).*

* cited by examiner

*Primary Examiner* — Michael G. Hartley
*Assistant Examiner* — Sean R Donohue
(74) *Attorney, Agent, or Firm* — Gonzales Patent Services; Ellen M. Gonzales

(57) ABSTRACT

A probe comprising a biomarker-triggered moiety, a near infrared (NIR) fluorophore reporter, a self-immolative linker and a self-immobilizing moiety for visualization of senescent cells and methods of use thereof.

3 Claims, 15 Drawing Sheets

$R^1$ = H, Et, $CH_2CH_2SO_3^-$, $CH_2CH_2CH_2SO_3^-$
$R^2$ = H, Cl $R^1$ = H, Et, $CH_2CH_2SO_3^-$, $CH_2CH_2CH_2SO_3^-$
$R^2$ = H, Cl

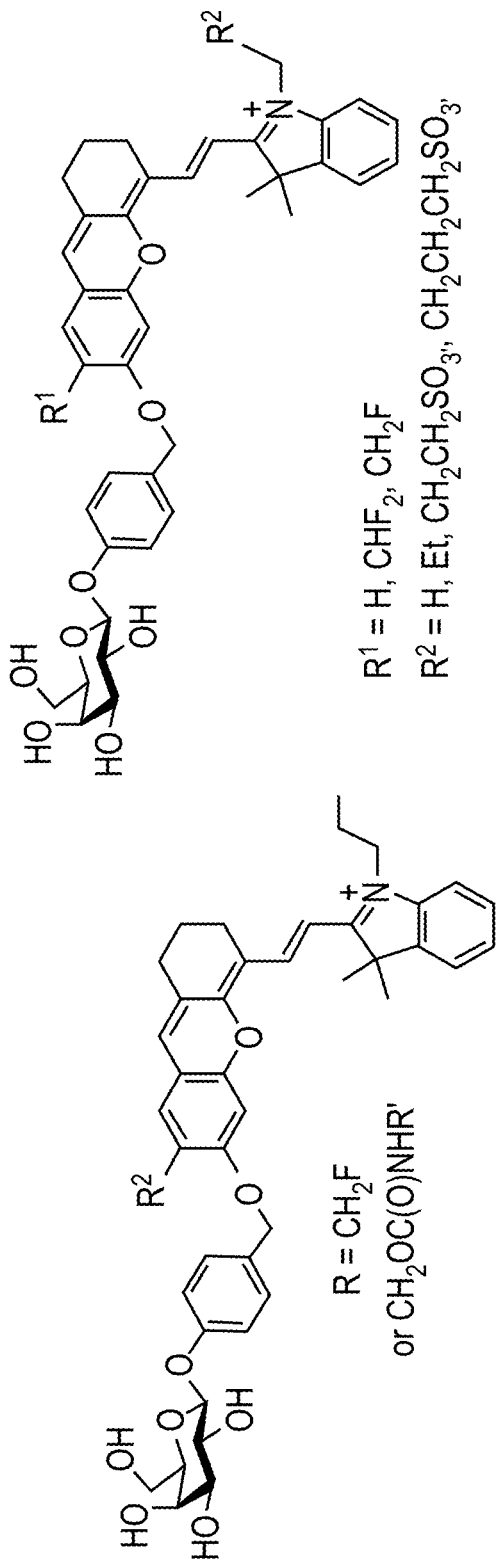
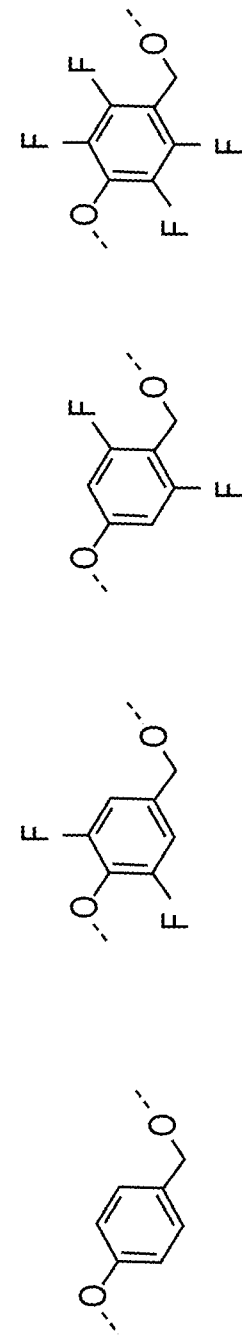

NEAR INFRARED SMALL MOLECULE PROBES FOR THE DETECTION OF CELLULAR SENESCENCE

CROSS-REFERENCE TO RELATED APPLICATIONS

The following application claims benefit of U.S. Provisional Application No. 62/828,242, filed Apr. 2, 2019, which is hereby incorporated by reference in its entirety.

STATEMENT REGARDING GOVERNMENT SPONSORED RESEARCH

This invention was made with Government support under Grant No. R35 GM124963 awarded by National Institutes of Health (NIH). The U.S. Government has certain rights in this invention.

BACKGROUND

Cellular senescence, a process that halts cell cycle, is a cellular stress response to various stimuli including telomere erosion, DNA damage, chromatin perturbation, activation of oncogenes,[1-4] and increasing evidences revealed that senescence is implicated in aging and age-related diseases[3-4]. Senescence is regularly characterized by morphological changes in vitro and the overexpression of cell cycle inhibitors, such as p16, p21 and p53,[2, 5] as well as senescence-associated β-galactosidase (SA-β-Gal), which is derived from the increased lysosomal content of senescent cells[5-6]. Monitoring the status of cellular senescence in living subjects allows the study of senescence in real-time without the need to end the experiments, enabling long-term study of senescence-related disease progression, and evaluation of treatment responses of both regular cancer therapies and senescence-targeted therapies.

Most fluorescent probes[7-10 17] developed for β-gal detection in live cells with a reporter lacZ(+) gene can potentially be used for senescence detection, and some[11-12 13] have been applied for the detection of SA-β-Gal. For example, the routinely used substrate X-Gal (5-bromo-4-chloro-3-indolyl-β-D-galactoside) yields a blue insoluble indigoid dye in the presence of β-gal, making it suitable for β-gal detection via histochemical staining in vitro[39]. Pioneered by Nagano and Urano, a series of fluorescein and rhodamine derived probes have been developed for β-gal detection in LacZ(+) live cells[7,8,26,40]. Near infrared (NIR) fluorescence is favored for in vivo studies due to the decreased tissue autofluorescence, high penetration depth, and low light scattering[41]. Weissleder and colleagues developed a far red fluorescence probe DDAOG, a β-galactoside of 7-hydroxy-9H-(1,3-dichloro-9,9-dimethylacridin-2-one), for the detection of LacZ(+) model tumor in vivo[42]. A bioluminescent probe, a conjugate of β-galactoside and luciferin, allowed detection of β-gal in a mice model injected with engineered cell line expressing both LacZ and fLuc (encoding firefly luciferase)[43]. Via photoacoustic imaging, Wang and coworkers were able to detect β-gal activity in LacZ(+) cells in vivo using X-Gal as substrate[44]. Recently, a couple of groups showed the detection of endogenous β-gal in several rare cases of cancers. For example, Urano and colleagues applied their fluorogenic probe hydroxymethyl rhodol (HMR) β-galactoside, with 1,400-fold fluorescence turn-on ratio, for visualization of small peritoneal metastatic tumors[45]. A ratiometric near-infrared fluorescent probe was developed for real-time tracking and imaging of β-gal activity in colorectal tumor in vivo[17]. However, novel probes that enable visualization of senescent cells in vivo are greatly desired.

SUMMARY

A probe comprising a biomarker-triggered moiety, a near infrared (NIR) fluorophore reporter, a self-immolative linker and a self-immobilizing moiety for visualization of senescent cells and methods of use thereof.

BRIEF DESCRIPTION OF THE DRAWINGS

FIG. 5 is the chemical structure of still another probe according to an embodiment of the present disclosure.

FIG. 6 is the chemical structure of yet another probe according to an embodiment of the present disclosure.

FIG. 7 is the chemical structure of a portion of the probe is FIGS. 3 and 4.

FIG. 8 is a substitute chemical structure for the structure shown in FIG. 7.

FIG. 9 is another substitute chemical structure for the structure shown in FIG. 7.

FIG. 10 is still another substitute chemical structure for the structure shown in FIG. 7.

DETAILED DESCRIPTION

Figure 1:
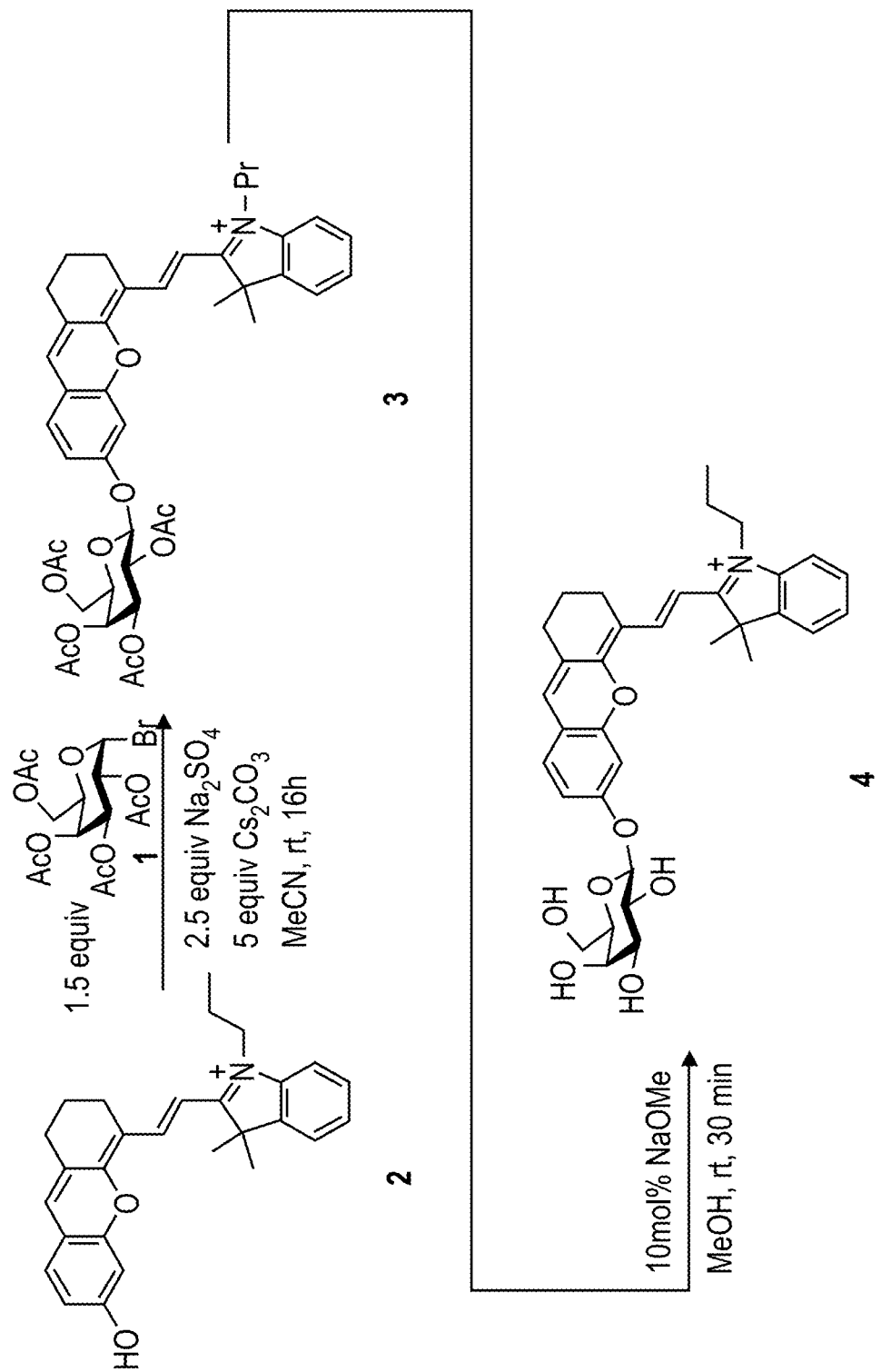
FIG. 1 is an exemplary synthesis scheme for a probe according to an embodiment of the present disclosure.

According to an embodiment the present disclosure provides a novel probe that enables the in vivo visualization of senescent cells. In general, the probe of the present disclosure comprises or consists of four moieties: a biomarker-triggered moiety, a near infrared (NIR) fluorophore reporter, a self-immolative linker and a self-immobilizing moiety. According to an embodiment, the fluorescence of the probe is designed to "turn-on" in the presence of one or more senescence-associated biomarkers such as, for example, senescence-associated β-gal (SABG).

Those of skill in the art will be familiar with a wide variety of biomarker-triggered moieties. Examples of suitable biomarker-triggered moieties include, but are not limited to, 0-galactosidase-triggered moieties including, but not limited to β-galactose. Additional information, including additional suitable biomarkers and biomarker triggered moieties may be obtained from the references incorporated by reference below and, in particular, references 5, 6, 13 and 38.

NIR fluorophores are fluorophores with excitation and emission spectra in the near infrared range. Examples of suitable NIR fluorophore reporters include, but are not limited to, hemicyanine derivatives (see attached chemdraw file). Hemicyanine derivatives, for example, have excellent stability, low toxicity, and fluorescence emission in NIR range upon activation[19]. The fluorophore has demonstrated its suitability for fluorescence imaging of various biomolecules, such as the detection of β-Lactamase in *Staphylococcus aureus*[20], the detection of nitroxyl (HNO)[21] and palladium[22] in live cells, the detection of nitroreductase[23], γ-glutamyl transpeptidase[24] and tyrosinase[25] in zebrafish. More recently, the hemicyanine NIR dyes have been used for in vivo detection of cysteine[26,27], alkaline phosphatase in tumor models[28-30], superoxide radical anion[31], hydrogen sulphide[32], hydrogen polysulfides[33] and γ-glutamyl transpeptidase[34] in mice models. A specific example of an NIR fluorophore is (E)-2-(2-(6-hydroxy-2,3-dihydro-1H-xanthen-4-yl)vinyl)-3,3-dimethyl-1-propyl-3H-indol-1-ium (HXPI). Additional information, including additional suitable fluorophores and NIR fluorophores can be found, for example, in the references incorporated by reference below, including, but not limited to, references 7-11, 13-17, 25, 29, 31-34, and 40-57.

Self-immolative linkers are typically moieties which disassemble or degrade, typically spontaneously or in response to a an activation event. An example of a self-immolative linker is 4-(hydroxymethyl)phenol. Other examples of suitable self-immolative linkers include, but are not limited to, the structure containing substituents on the phenyl ring of 4-(hydroxymethyl)phenol. Additional information on self-immolative linkers, including additional suitable linkers may be obtained from the references incorporated by reference below including, but not limited to references 12 and 21.

Suitable self-immobilizing moieties include —$CH_2F$, —$CHF_2$, and $CH2OC(O)NHR'$ (See, e.g., ref. 40.) Additional information on self-immobilizing moities, including additional suitable moities may be obtained from the references incorporated by reference below including, but not limited to reference 40.

According to an embodiment, the probe may be synthesized by glycosylation of a hemicyanine dye and a protected galactosyl bromide, followed by a deprotection step. (For clarity in the present disclosure, the abbreviation "NIR-BG" refers to probes synthesized using this method.) FIG. 1 provides an exemplary synthesis scheme according to an embodiment. (For clarity in the present disclosure, the abbreviation "NIR-BG" refers to probes synthesized using this method.) Compound 3 was produced by stirring a solution of compounds 1 (49.3 mg, 0.12 mmol) and 2 (43 mg, 0.08 mmol) in 3 mL of MeCN at room temperature. $Na_2SO_4$ (28.4 mg, 0.2 mmol) and $Cs_2CO3$ (130 mg, 0.4 mmol) were added, and the reaction mixture was stirred at room temperature in the dark for 16 h. Then this mixture was then filtered through a Celite pad and concentrated. The residue was purified by HPLC to afford 3 (25.7 mg, 38%) $^1$H NMR (500 MHz, $CDCl_3$) δ 8.68 (d, J=14.5 Hz, 1H), 7.55-7.49 (m, 2H), 7.45-7.36 (m, 3H), 7.18 (s, 1H), 6.98-6.96 (m, 2H), 6.48 (d, J=14.5 Hz, 1H), 5.55-5.12 (m, 2H), 5.33-5.31 (m, 1H), 5.21-5.19 (m, 1H), 4.31-4.28 (m, 3H), 4.25-4.22 (m, 1H), 4.15-4.11 (m, 1H), 2.76-2.74 (m, 2H), 2.68-2.67 (s, 2H), 2.20 (s, 3H), 2.11 (s, 3H), 2.06 (s, 3H), 2.04 (s, 3H), 1.98-1.94 (m, 4H), 1.82 (s, 6H), 1.07 (t, J=7.5 Hz, 3H). $^{13}$C NMR (126 MHz, $CDCl_3$) δ 178.21, 170.50, 170.23, 170.08, 169.82, 161.25, 159.29, 153.95, 146.36, 142.08, 141.48, 132.80, 129.39, 128.90, 128.77, 127.80, 122.70, 117.67, 115.15, 113.90, 112.88, 104.58, 98.65, 71.18, 70.82, 68.58, 66.84, 61.09, 51.00, 47.08, 29.82, 29.33, 28.28, 28.18, 24.03, 21.42, 20.89, 20.79, 20.68, 20.25, 11.48. HRMS (ESI) Calcd. For $C42H48NO11^+[M]^+$: 742.3222; found: 742.3243. In order to produce compound 4, 0.7 µL of 25% NaOMe in MeOH was added to a solution of compound 3 (25.7 mg, 0.03 mmol) in 1 mL of MeOH. The mixture was stirred at room temperature for 30 min. Then the mixture was purified by HPLC to afford 4 (19.4 mg, 94%). $^1$H NMR (500 MHz, $CD_3OD$) δ=8.81 (d, J=15.0 Hz, 1H), 7.68 (d, J=7.5 Hz, 1H), 7.59-7.52 (m, 2H), 7.49-7.45 (m, 2H), 7.38 (s, 1H), 7.22 (s, 1H), 7.12 (d, J=8.5, 1H), 6.55 (d, J=15.0 Hz, 1H), 5.02 (d, J=7.5 Hz, 1H), 4.35 (t, J=7.0 Hz, 2H), 3.95 (d, J=2.5 Hz, 1H), 3.88-3.80 (m, 4H), 3.64 (dd, J=10.0 Hz, 2.0 Hz, 1H), 2.79 (t, J=5.0 Hz, 2H), 2.72 (d, J=6.0 Hz, 2H), 1.98-1.94 (m, 4H), 1.85 (s, 3H), 1.83 (s, 3H), 1.08 (t, J=7.5 Hz, 3H). $^{13}$C NMR (126 MHz, $CD_3OD$) δ=179.71, 162.78, 162.32, 155.43, 147.39, 143.66, 142.99, 134.51, 130.23, 129.87, 129.26, 128.55, 123.84, 118.27, 116.33, 115.66, 114.09, 105.20, 104.70, 102.99, 77.67, 74.79, 72.07, 70.28, 62.66, 52.17, 47.59, 30.11, 28.41, 28.32, 24.97, 22.31, 21.62, 11.57. HRMS (ESI) Calcd. For $C_{34}H_{40}NO_7^+$ $[M]^+$: 574.2799; found: 574.2803.

Figure 2:
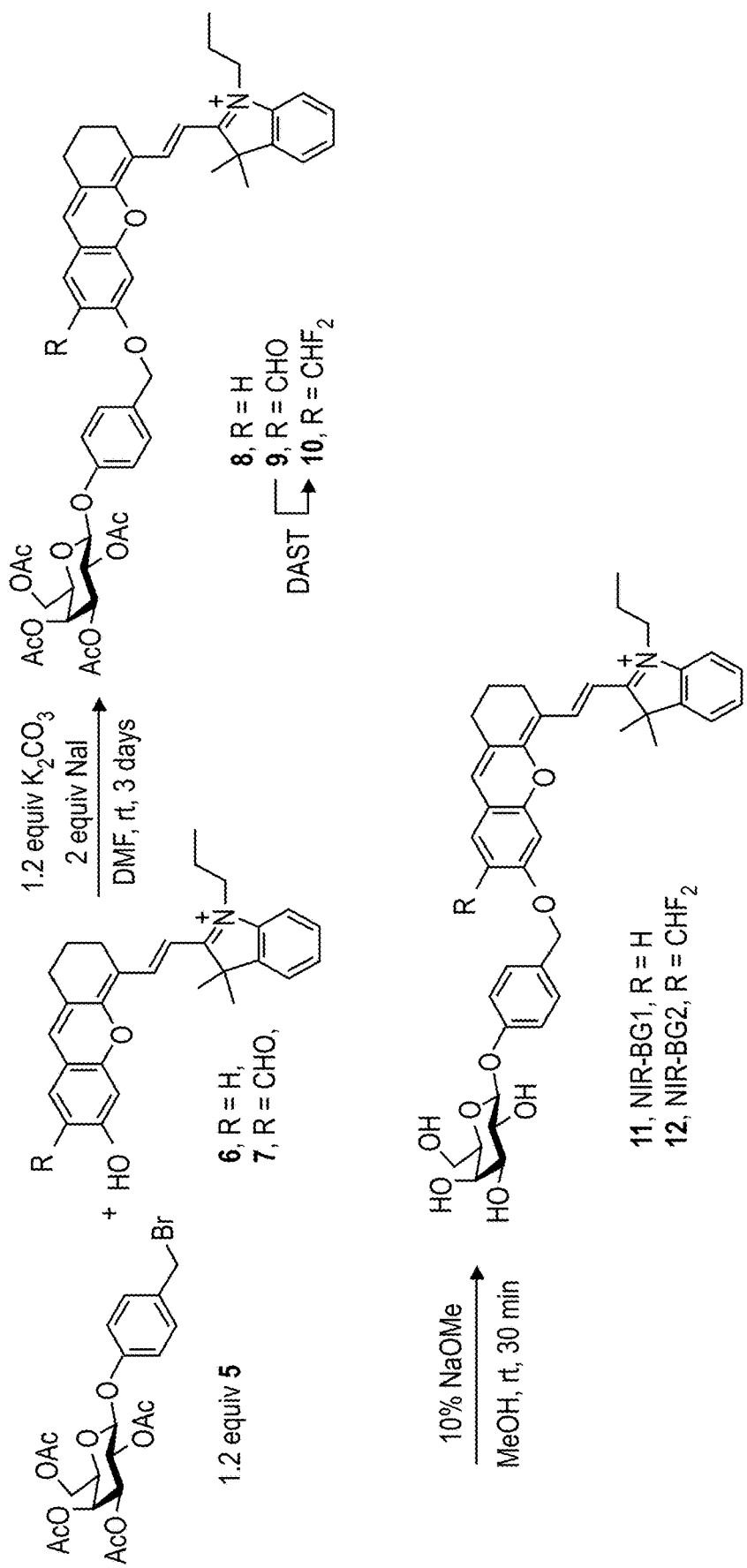
FIG. 2 is an alternative synthesis scheme for a probe according to an embodiment of the present disclosure.
Figure 4:
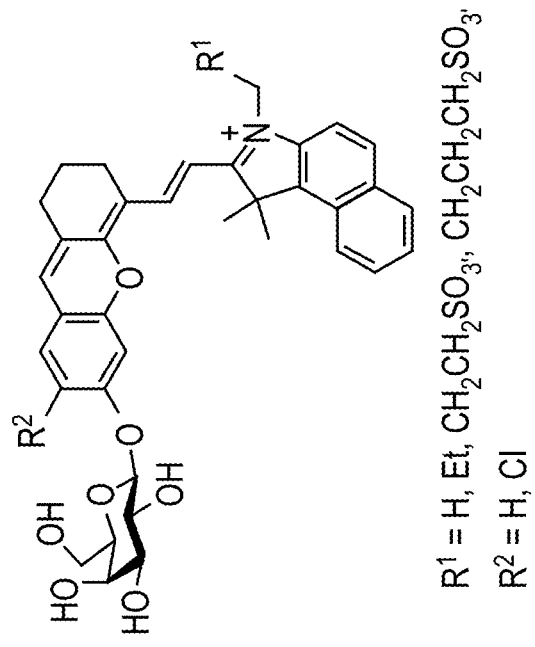
FIG. 4 is the chemical structure of another probe according to an embodiment of the present disclosure.
Figure 3:
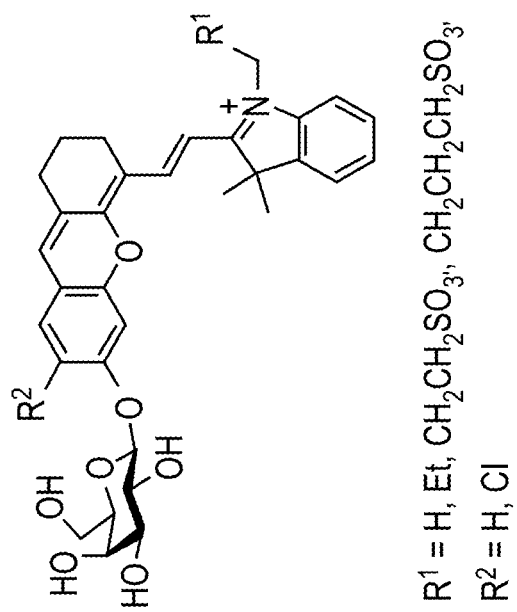
FIG. 3 is the chemical structure of a probe according to an embodiment of the present disclosure.

An alternative synthesis scheme is shown in FIG. 2, which provides for the synthesis of NIR-BG1, a control probe which lacks the immobilizing group and NIR-BG2. These probes were obtained by incorporating acetyl galactose substituted benzyl moieties into the corresponding NIR fluorophore and global removal of acetyl groups. For the probe NIR-BG2, fluorination of aldehyde is required prior to deprotection of acetyl groups.

Additional suitable probes are shown in FIGS. 3-6. In the structures shown in FIGS. 5 and 6, the structure shown in FIG. 7 can be replaced with any of the structures shown in FIGS. 8-10.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a probe" includes a plurality of such probes, and so forth.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

REFERENCES

1. Campisi, J.; d'Adda di Fagagna, F., Cellular senescence: when bad things happen to good cells. Nature reviews. Molecular cell biology 2007, 8 (9), 729-40.
2. Munoz-Espín, D.; Serrano, M., Cellular senescence: from physiology to pathology. Nature Reviews Molecular Cell Biology 2014, 15, 482.
3. Childs, B. G.; Durik, M.; Baker, D. J.; van Deursen, J. M., Cellular senescence in aging and age-related disease: from mechanisms to therapy. Nat Med 2015, 21 (12), 1424-1435.
4. van Deursen, J. M., The role of senescent cells in ageing. Nature 2014, 509, 439.
5. Collado, M.; Serrano, M., The power and the promise of oncogene-induced senescence markers. Nature Reviews Cancer 2006, 6 (6), 472-476.
6. Dimri, G. P.; Lee, X. H.; Basile, G.; Acosta, M.; Scott, C.; Roskelley, C.; Medrano, E. E.; Linskens, M.; Rubelj, I.; Pereirasmith, O.; Peacocke, M.; Campisi, J., A Biomarker That Identifies Senescent Human-Cells in Culture and in Aging Skin in-Vivo. P Natl Acad Sci USA 1995, 92 (20), 9363-9367.
7. Urano, Y.; Kamiya, M.; Kanda, K.; Ueno, T.; Hirose, K.; Nagano, T., Evolution of fluorescein as a platform for finely tunable fluorescence probes. Journal of the American Chemical Society 2005, 127 (13), 4888-4894.
8. Kamiya, M.; Asanuma, D.; Kuranaga, E.; Takeishi, A.; Sakabe, M.; Miura, M.; Nagano, T.; Urano, Y., beta-Galactosidase Fluorescence Probe with Improved Cellular Accumulation Based on a Spirocyclized Rhodol Scaffold. Journal of the American Chemical Society 2011, 133 (33), 12960-12963.
9. Sakabe, M.; Asanuma, D.; Kamiya, M.; Iwatate, R. J.; Hanaoka, K.; Terai, T.; Nagano, T.; Urano, Y., Rational Design of Highly Sensitive Fluorescence Probes for Protease and Glycosidase Based on Precisely Controlled Spirocyclization. Journal of the American Chemical Society 2013, 135 (1), 409-414.
10. Egawa, T.; Koide, Y.; Hanaoka, K.; Komatsu, T.; Terai, T.; Nagano, T., Development of a fluorescein analogue, TokyoMagenta, as a novel scaffold for fluorescence probes in red region. Chemical communications 2011, 47 (14), 4162-4.
11. Safir, M.; Dao, P.; Gesson, M.; Martin, A. R.; Benhida, R., Development of highly sensitive fluorescent probes for the detection of beta-galactosidase activity—application to the real-time monitoring of senescence in live cells. Analyst 2018, 143 (11), 2680-2688.
12. Chen, X. Z.; Ma, X. D.; Zhang, Y. Y.; Gao, G.; Liu, J. J.; Zhang, X. Y.; Wang, M. A.; Hou, S. C., Ratiometric fluorescent probes with a self-immolative spacer for real-time detection of beta-galactosidase and imaging in living cells. Anal Chim Acta 2018, 1033, 193-198.
13. Lozano-Torres, B.; Galiana, I.; Rovira, M.; Garrido, E.; Chaib, S.; Bernardos, A.; Munoz-Espin, D.; Serrano, M.; Martinez-Manez, R.; Sancenon, F., An OFF-ON Two-Photon Fluorescent Probe for Tracking Cell Senescence in Vivo. Journal of the American Chemical Society 2017, 139 (26), 8808-8811.
14. Yuan, L.; Lin, W. Y.; Zheng, K. B.; He, L. W.; Huang, W. M., Far-red to near infrared analyte-responsive fluorescent probes based on organic fluorophore platforms for fluorescence imaging. Chem Soc Rev 2013, 42 (2), 622-661.
15. Owens, E. A.; Henary, M.; El Fakhri, G.; Choi, H. S., Tissue-Specific Near-Infrared Fluorescence Imaging. Acc Chem Res 2016, 49 (9), 1731-40.

16. Guo, Z.; Park, S.; Yoon, J.; Shin, I., Recent progress in the development of near-infrared fluorescent probes for bioimaging applications. Chem Soc Rev 2014, 43 (1), 16-29.
17. Gu, K. Z.; Xu, Y. S.; Li, H.; Guo, Z. Q.; Zhu, S. J.; Zhu, S. Q.; Shi, P.; James, T. D.; Tian, H.; Zhu, W. H., Real-Time Tracking and In Vivo Visualization of beta-Galactosidase Activity in Colorectal Tumor with a Ratiometric Near-Infrared Fluorescent Probe. Journal of the American Chemical Society 2016, 138 (16), 5334-5340.
18. Wang, Y.; Liu, J.; Ma, X. W.; Cui, C.; Deenik, P. R.; Henderson, P. K. P.; Sigler, A. L.; Cui, L., Real-time imaging of senescence in tumors with DNA damage. Sci Rep-Uk 2019, 9.
19. Halazy, S.; Berges, V.; Ehrhard, A.; Danzin, C., Ortho- and para-(difluoromethyl)aryl-β-d-glucosides: A new class of enzyme-activated irreversible inhibitors of 0-glucosidases. Bioorg Chem 1990, 18 (3), 330-344.
20. Myers, J. K.; Widlanski, T. S., MECHANISM-BASED INACTIVATION OF PROSTATIC ACID-PHOSPHATASE. Science 1993, 262 (5138), 1451-1453.
21. Kwan, D. H.; Chen, H. M.; Ratananikom, K.; Hancock, S. M.; Watanabe, Y.; Kongsaeree, P. T.; Samuels, A. L.; Withers, S. G., Self-immobilizing fluorogenic imaging agents of enzyme activity. Angewandte Chemie 2011, 50 (1), 300-3.
22. Doura, T.; Kamiya, M.; Obata, F.; Yamaguchi, Y.; Hiyama, T. Y.; Matsuda, T.; Fukamizu, A.; Noda, M.; Miura, M.; Urano, Y., Detection of LacZ-Positive Cells in Living Tissue with Single-Cell Resolution. Angewandte Chemie 2016, 55 (33), 9620-4.
23. Gao, Z.; Thompson, A. J.; Paulson, J. C.; Withers, S. G., Proximity Ligation-Based Fluorogenic Imaging Agents for Neuraminidases. Angewandte Chemie 2018.
24. Mao, W. Y.; Xia, L. Y.; Wang, Y. Q.; Xie, H. X., A Self-Immobilizing and Fluorogenic Probe for—Lactamase Detection. Chem-Asian J 2016, 11 (24), 3493-3497.
25. Yuan, L.; Lin, W. Y.; Zhao, S.; Gao, W. S.; Chen, B.; He, L. W.; Zhu, S. S., A Unique Approach to Development of Near-Infrared Fluorescent Sensors for in Vivo Imaging. Journal of the American Chemical Society 2012, 134 (32), 13510-13523.
26. Burke, H. M.; Gunnlaugsson, T.; Scanlan, E. M., Recent advances in the development of synthetic chemical probes for glycosidase enzymes. Chemical communications 2015, 51 (53), 10576-10588.
27. Karton-Lifshin, N.; Segal, E.; Omer, L.; Portnoy, M.; Satchi-Fainaro, R.; Shabat, D., A Unique Paradigm for a Turn-ON Near-Infrared Cyanine-Based Probe: Noninvasive Intravital Optical Imaging of Hydrogen Peroxide. Journal of the American Chemical Society 2011, 133 (28), 10960-10965.
28. Redy-Keisar, O.; Kisin-Finfer, E.; Ferber, S.; Satchi-Fainaro, R.; Shabat, D., Synthesis and use of QCy7-derived modular probes for the detection and imaging of biologically relevant analytes. Nat Protoc 2014, 9 (1), 27-36.
29. Fang, Y.; Chen, W.; Shi, W.; Li, H.; Xian, M.; Ma, H., A near-infrared fluorescence off-on probe for sensitive imaging of hydrogen polysulfides in living cells and mice in vivo. Chemical communications 2017, 53 (62), 8759-8762.
30. Wu, X.; Li, L.; Shi, W.; Gong, Q.; Ma, H., Near-Infrared Fluorescent Probe with New Recognition Moiety for Specific Detection of Tyrosinase Activity: Design, Synthesis, and Application in Living Cells and Zebrafish. Angewandte Chemie 2016, 55 (47), 14728-14732.
31. Ning, J.; Liu, T.; Dong, P.; Wang, W.; Ge, G.; Wang, B.; Yu, Z.; Shi, L.; Tian, X.; Huo, X.; Feng, L.; Wang, C.; Sun, C.; Cui, J. N.; James, T. D.; Ma, X., A molecular design strategy to construct the near-infrared fluorescent probe for selectively sensing human cytochrome P450 2J2. Journal of the American Chemical Society 2018.
32. Wrobel, A. T.; Johnstone, T. C.; Deliz Liang, A.; Lippard, S. J.; Rivera-Fuentes, P., A fast and selective near-infrared fluorescent sensor for multicolor imaging of biological nitroxyl (HNO). Journal of the American Chemical Society 2014, 136 (12), 4697-705.
33. Tan, Y.; Zhang, L.; Man, K. H.; Peltier, R.; Chen, G.; Zhang, H.; Zhou, L.; Wang, F.; Ho, D.; Yao, S. Q.; Hu, Y.; Sun, H., Reaction-Based Off-On Near-infrared Fluorescent Probe for Imaging Alkaline Phosphatase Activity in Living Cells and Mice. ACS Appl Mater Interfaces 2017, 9 (8), 6796-6803.
34. Li, L. H.; Li, Z.; Shi, W.; Li, X. H.; Ma, H. M., Sensitive and Selective Near-Infrared Fluorescent Off-On Probe and Its Application to Imaging Different Levels of beta-Lactamase in *Staphylococcus aureus*. Anal Chem 2014, 86 (12), 6115-6120.
35. te Poele, R. H., Okorokov, A. L., Jardine, L., Cummings, J. & Joel, S. P. DNA damage is able to induce senescence in tumor cells in vitro and in vivo. Cancer Research 62, 1876-1883 (2002).
36. Wong, R. S. Y. Apoptosis in cancer: from pathogenesis to treatment. Journal of Experimental & Clinical Cancer Research 30, doi:10.1186/1756-9966-30-87 (2011).
37. Jackson, S. P. & Bartek, J. The DNA-damage response in human biology and disease. Nature 461, 1071-1078, doi:10.1038/nature08467 (2009).
38. Kurz, D. J., Decary, S., Hong, Y. & Erusalimsky, J. D. Senescence-associated beta-galactosidase reflects an increase in lysosomal mass during replicative ageing of human endothelial cells. Journal of Cell Science 113, 3613-3622 (2000).
39. Horwitz, J. P. et al. Substrates for Cytochemical Demonstraton of Enzyme Activity 0.1. Some Substituted 3-Indolyl-Beta-D_Glycopyranosides. Journal of Medicinal Chemistry 7, 574-&, doi:10.1021/jm00334a044 (1964).
40. Komatsu, T. et al. Design and synthesis of an enzyme activity-based labeling molecule with fluorescence spectral change. Journal of the American Chemical Society 128, 15946-15947, doi:10.1021/ja0657307 (2006).
41. Weissleder, R. & Pittet, M. J. Imaging in the era of molecular oncology. Nature 452, 580-589, doi:10.1038/nature06917 (2008).
42. Tung, C. H. et al. In vivo imaging of beta-galactosidase activity using far red fluorescent switch. Cancer Research 64, 1579-1583, doi:10.1158/0008-5472.can-03-3226 (2004).
43. Wehrman, T. S., von Degenfeld, G., Krutzik, P., Nolan, G. P. & Blau, H. M.
Luminescent imaging of beta-galactosidase activity in living subjects using sequential reporter-enzyme luminescence. Nature Methods 3, 295-301, doi:10.1038/nmeth868 (2006).
44. Li, L., Zemp, R. J., Lungu, G., Stoica, G. & Wang, L. V. Photoacoustic imaging of lacZ gene expression in vivo. Journal of Biomedical Optics 12, doi:10.1117/1.2717531 (2007).
45. Asanuma, D. et al. Sensitive beta-galactosidase-targeting fluorescence probe for visualizing small peritoneal metastatic tumours in vivo. Nature Communications 6, doi: 10.1038/ncomms7463 (2015).

Figure 11:
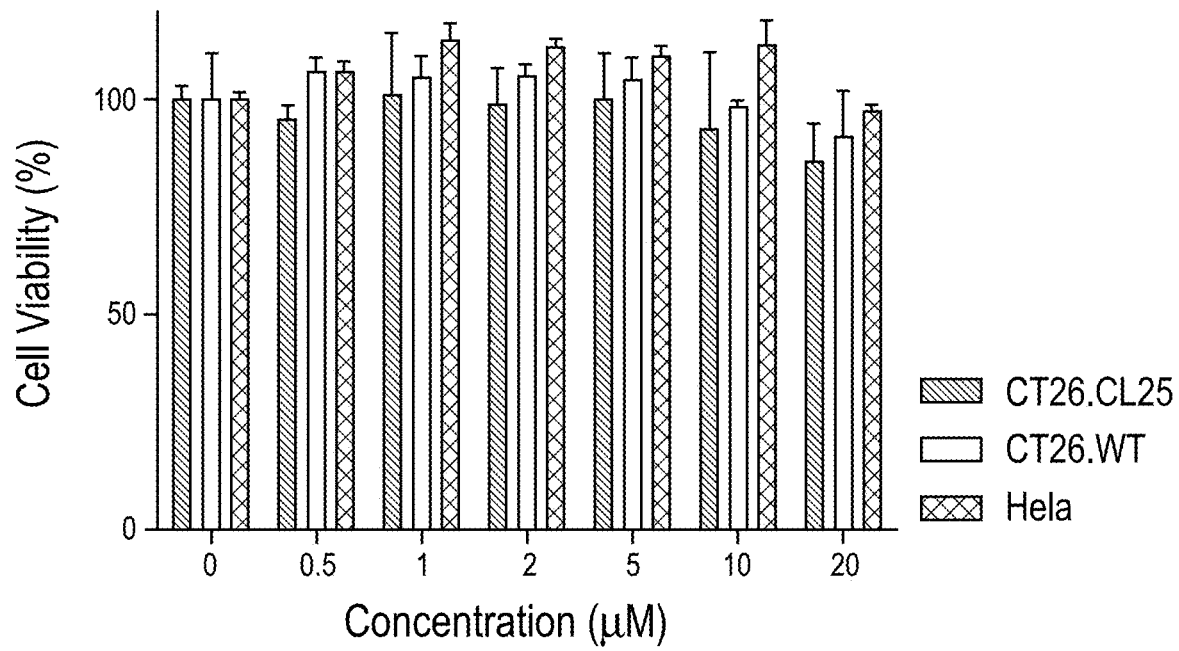
FIG. 11 is a graph showing cell viability of the cells in the study after incubation with the NIR-BG probe for 4 hours.
Figure 12:
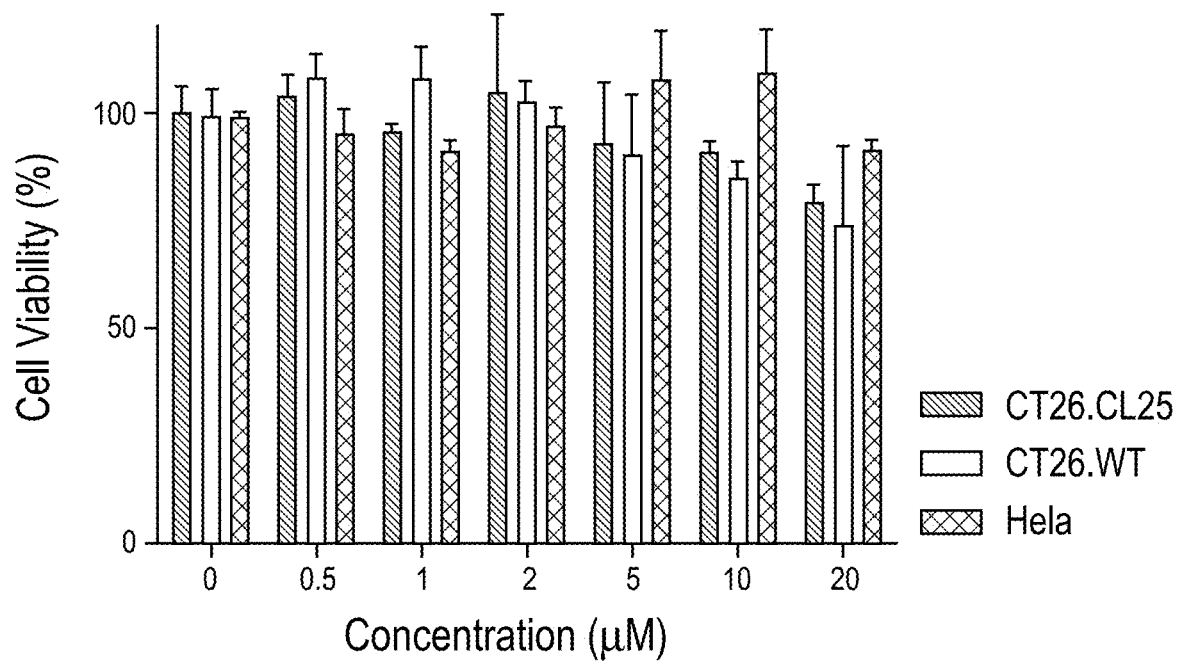
FIG. 12 is a graph showing cell viability of the cells in the study after incubation with the NIR-BG probe for 24 hours.
Figure 13:
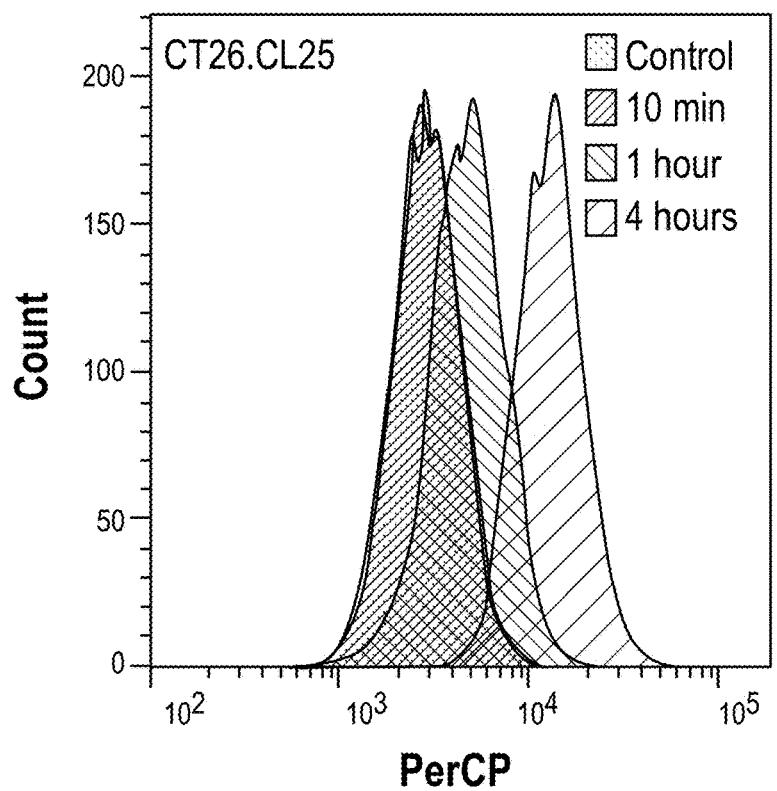
FIG. 13 is a graph showing flow cytometry detection of β-gal by the NIR-BG probe in LacZ(+) cells (CT26.CL25) probe (10 μM), $\lambda_{ex}$=640 nm.
Figure 14:
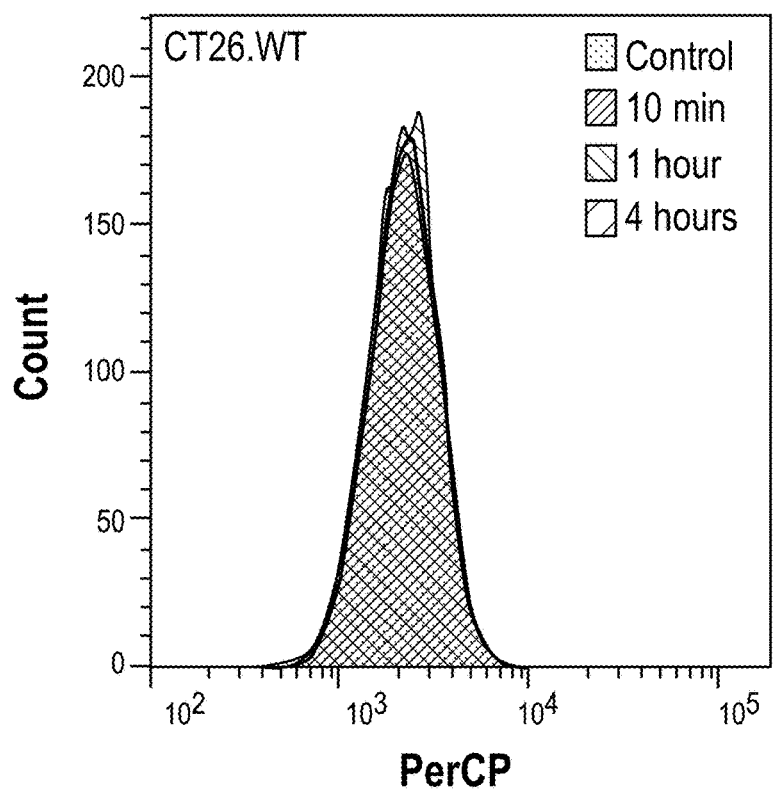
FIG. 14 is a graph showing flow cytometry detection of negative control CT26.WTcells probe (10 μM), $\lambda_{ex}$=640 nm.
Figure 15:
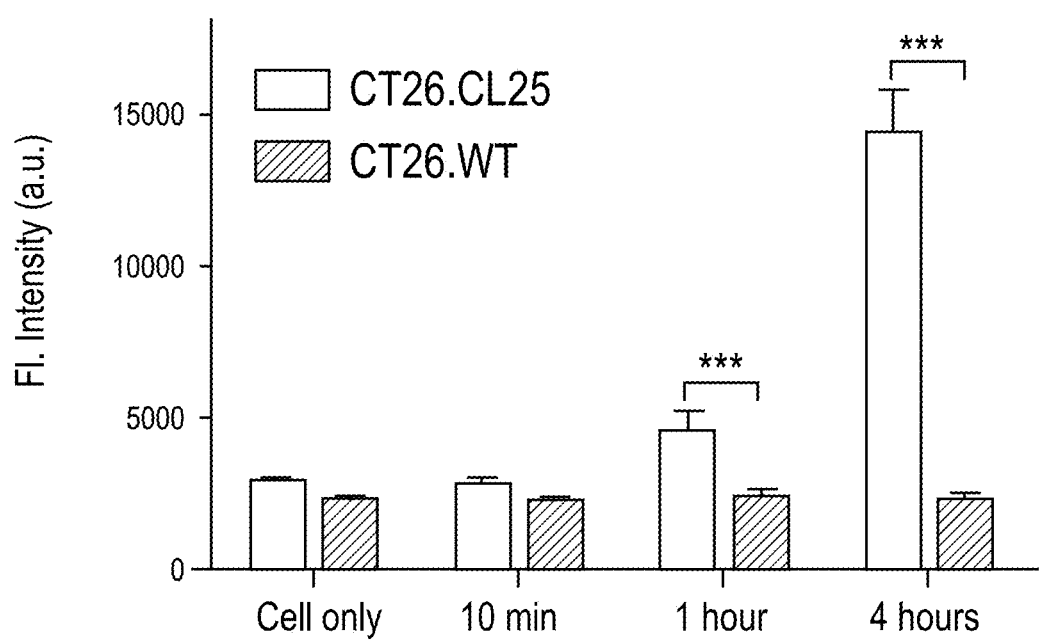
FIG. 15 depicts the quantification of the mean fluorescence intensity in FIGS. 13 and 14.
Figure 16:
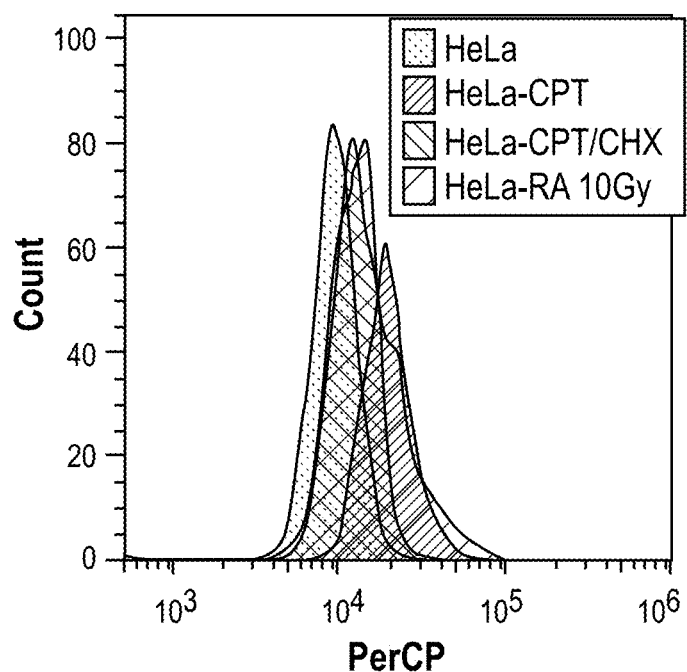
FIG. 16 is a graph showing detection of senescence in human cancer cells via flow cytometry of HeLa cells without treatment, or with CPT, CPT/CHX, or radiation treatment. Probe concentration, 10 μM. λex=640 nm; PerCP bandpass filter at 675/25 nm. ***P<0.001.
Figure 17:
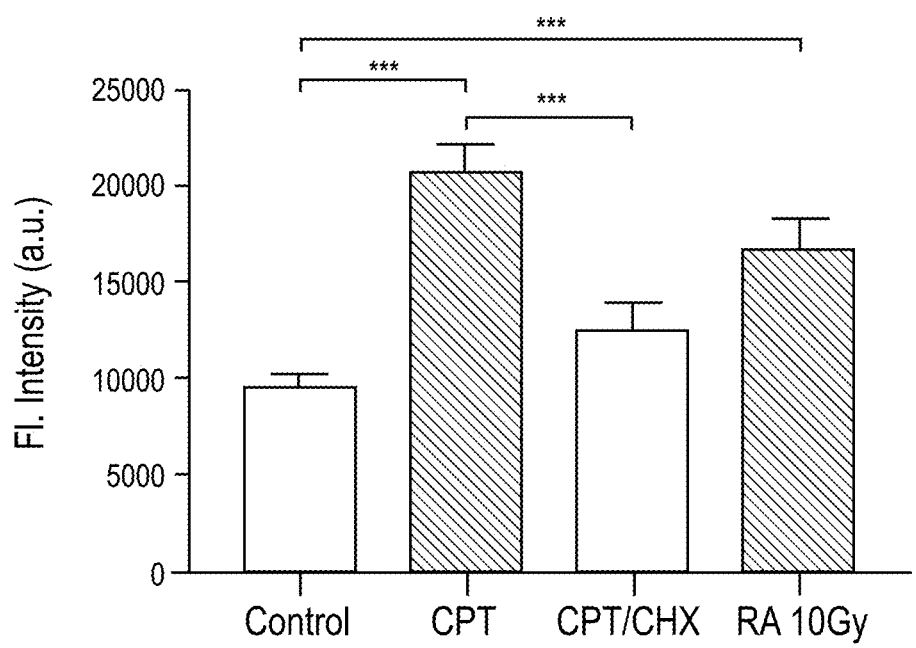
FIG. 17 is a quantification of FIG. 15.
Figure 18:
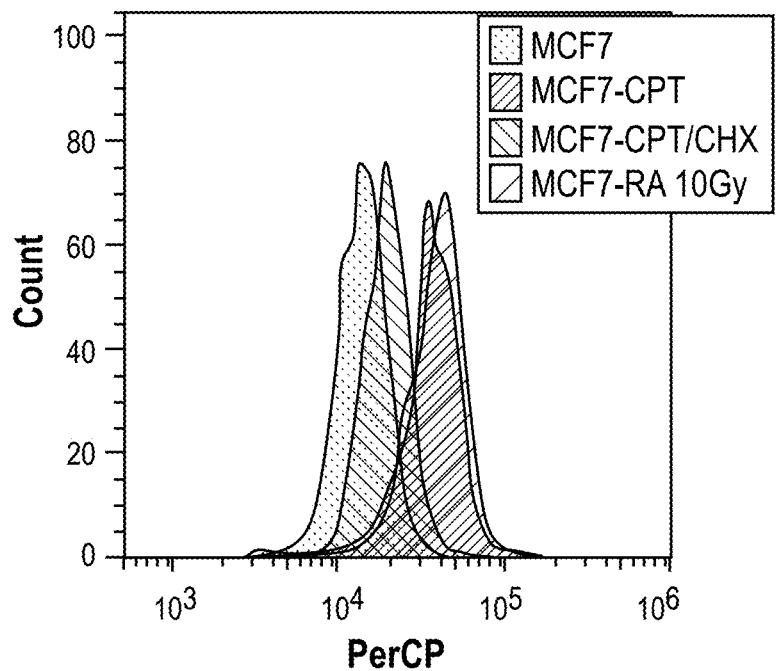
FIG. 18 is a graph showing Flow cytometry of MCF7 cells without treatment, or with CPT, CPT/CHX, or radiation treatment. Probe concentration, 10 μM. λex=640 nm; PerCP bandpass filter at 675/25 nm. ***P<0.001.
Figure 19:
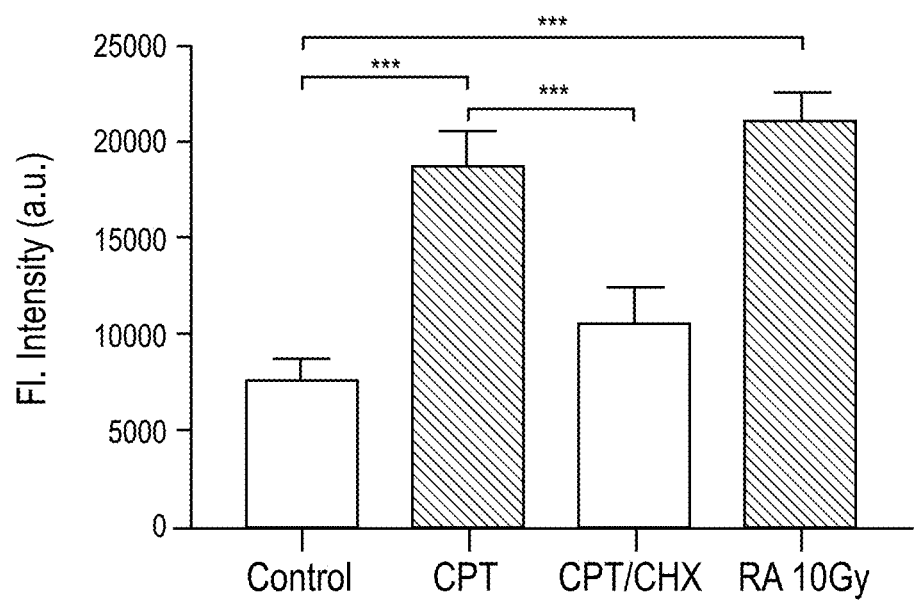
FIG. 19 is a quantification of FIG. 18.
Figure 20:
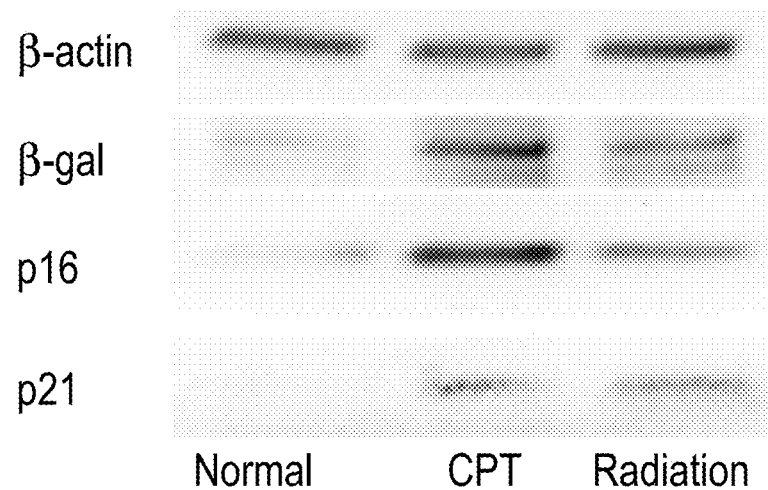
FIG. 20 is a western blot of cell lysates of β-gal, p16, and p21 expression in HeLa cells without drug treatment, with CPT or radiation treatment. *P<0.001, P<0.005.
Figure 21:
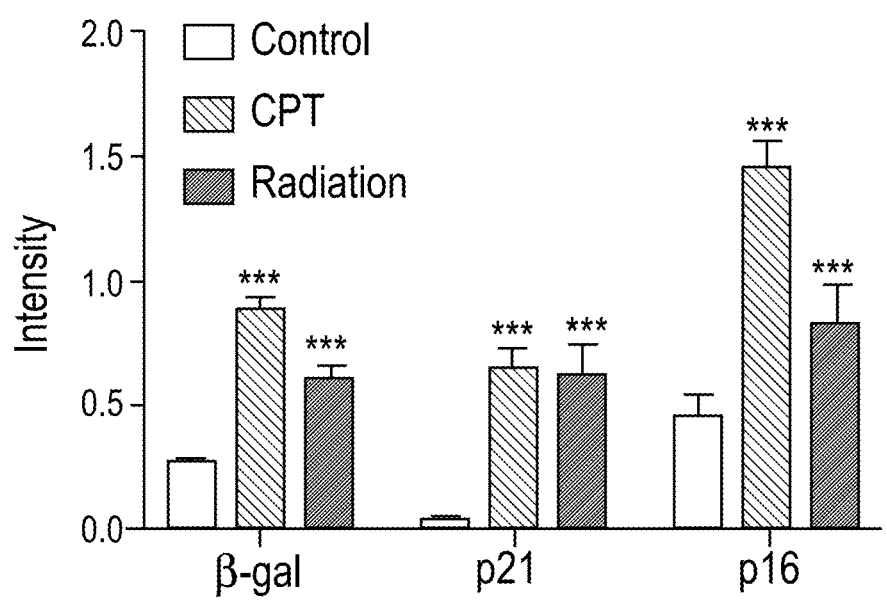
FIG. 21 is a quantification of FIG. 20.

46. Su, W. et al. A near-infrared and colorimetric fluorescent probe for palladium detection and bioimaging. Dyes and Pigments 137, 293-298, doi:10.1016/j.dyepig.2016.10.052 (2017).
47. Li, Z. et al. in vivo imaging and detection of nitroreductase in zebrafish by a new near-infrared fluorescence off-on probe. Biosens Bioelectron 63, 112-116, doi:10.1016/j.bios.2014.07.024 (2015).
48. Li, L. H. et al. Monitoring gamma-glutamyl transpeptidase activity and evaluating its inhibitors by a water-soluble near-infrared fluorescent probe. Biosensors & Bioelectronics 81, 395-400, doi:10.1016/j.bios.2016.03.021 (2016).
49. Wu, X. F., Li, L. H., Shi, W., Gong, Q. Y. & Ma, H. M. Near-Infrared Fluorescent Probe with New Recognition Moiety for Specific Detection of Tyrosinase Activity: Design, Synthesis, and Application in Living Cells and Zebrafish. Angewandte Chemie-International Edition 55, 14728-14732, doi:10.1002/anie.201609895 (2016).
50. Zhang, J. J. et al. Near-Infrared and Naked-Eye Fluorescence Probe for Direct and Highly Selective Detection of Cysteine and Its Application in Living Cells. Analytical Chemistry 87, 4856-4863, doi:10.1021/acs.analchem.5600377 (2015).
51. Han, C. M. et al. Mitochondria-Targeted Near-Infrared Fluorescent Off-On Probe for Selective Detection of Cysteine in Living Cells and in Vivo. Acs Applied Materials & Interfaces 7, 27968-27975, doi:10.1021/acsami.5b10607 (2015).
52. Liu, H. W. et al. In vivo imaging of alkaline phosphatase in tumor-bearing mouse model by a promising near-infrared fluorescent probe. Talanta 175, 421-426, doi:https://doi.org/10.1016/j.talanta.2017.04.081 (2017).
53. Li, S. J. et al. Facile and Sensitive Near-Infrared Fluorescence Probe for the Detection of Endogenous Alkaline Phosphatase Activity In Vivo. Analytical Chemistry 89, 6854-6860, doi:10.1021/acs.analchem.7b01351 (2017).
54. Zhang, J. J. et al. A phosphinate-based near-infrared fluorescence probe for imaging the superoxide radical anion in vitro and in vivo. Chemical Communications 52, 2679-2682, doi:10.1039/c5cc09976e (2016).
55. Zhang, L. et al. A highly selective and sensitive near-infrared fluorescent probe for imaging of hydrogen sulphide in living cells and mice. Scientific Reports 6, doi:10.1038/srep18868 (2016).
56. Fang, Y. et al. A near-infrared fluorescence off-on probe for sensitive imaging of hydrogen polysulfides in living cells and mice in vivo. Chemical Communications 53, 8759-8762, doi:10.1039/c7cc04093h (2017).
57. Luo, Z. et al. Activatable Near-Infrared Probe for Fluorescence Imaging of γ-Glutamyl Transpeptidase in Tumor Cells and In Vivo. Chemistry—A European Journal, n/a-n/a, doi:10.1002/chem.201702210.
58. Lee, H. W. et al. Ratiometric Two-Photon Fluorescent Probe for Quantitative Detection of beta-Galactosidase Activity in Senescent Cells. Analytical Chemistry 86, 10001-10005, doi:10.1021/ac5031013 (2014).
59. Pommier, Y. Topoisomerase I inhibitors: camptothecins and beyond. Nat Rev Cancer 6, 789-802 (2006).
60. Takauji, Y. et al. Restriction of protein synthesis abolishes senescence features at cellular and organismal levels. Scientific Reports 6, doi:10.1038/srep18722 (2016).
61. Moog, K. E. et al. Polymeric Selectin Ligands Mimicking Complex Carbohydrates: From Selectin Binders to Modifiers of Macrophage Migration. Angewandte Chemie 56, 1416-1421, doi:10.1002/anie.201610395 (2017).
62. Wang, Y., Liu, J., Ma, X. et al. Real-time imaging of senescence in tumors with DNA damage. Sci Rep 9, 2102 (2019). https://doi.org/10.1038/s41598-019-38511-z Example 1—Detection of β-Gal in LacZ(+) Live Cells by NIR-BG In order to see whether our NIR-BG probe can be used for β-gal detection in live cells, we chose an engineered cell line that stably express LacZ(+), the gene that encodes β-gal. CT26.CL25, a mouse colon fibroblast carcinoma cell line that express β-gal, was therefore used in our initial live cell experiments. CT26.WT, the wild type cell line that does not express β-gal, was used as a control. Our probe did not appear toxic in either cell culture after 4 (FIG. 11) or 24-hours (FIG. 12) of incubation. Cell samples after incubating with our NIR-BG probe were analyzed using flow cytometry (FIG. 13-15) and confocal microscopy (not shown). Flow cytometry showed obvious fluorescence at 1 hour and 4 hours in CT26.CL25 cells incubated with our probe, whereas only background signal was detected in CT26.WT cells that received the same treatment. Confocal fluorescence microscopy images showed consistent results. Fluorescence signal was obvious in samples with 1-hour probe treatment, and the intensity increased with time in CT26.CL25 cells; while no fluorescence in the NIR channel was detected in the CT26.WT cells even after 4-hour incubation. The NIR signal in CT26.CL25 cells were highly colocalized with the β-gal expression. The fluorescence detected in CT26.CL25 cells using both flow cytometry and confocal microscopy was from our NIR-BG probe after hydrolysis of the galactose by β-gal while no fluorescence was detected in CT26.WT due to the lack of β-gal. The β-gal expression was confirmed by colorimetric X-gal staining (Not shown). Intensive blue stain was observed in CT26.CL25 cells, indicating high β-gal expression compared with the wild type cell line. Additional information and images can be found in Ref. 62.

Example 2—Imaging of Senescent State in Drug or Radiation Treated Human Cancer Cells by NIR-BG With the confidence of our probe being able to detect β-gal in live cells, we moved further to evaluate whether it could differentiate senescent cells and normal cells. Human cervical cancer cells (HeLa) and metastatic breast cancer cells (MCF7), were used in all four groups of cells evaluated. Senescence in HeLa and MCF7 cells were induced using camptothecin (CPT), an inhibitor of DNA topoisomerase I that could cause lethal DNA strand breaks[59]. Interestingly, when the cells were incubated with both CPT and cycloheximide (CHX), an experimental blocker of protein synthesis, cellular senescence could be alleviated[60]. Radiation therapy is another effective method for cancer treatment in clinic; it can also induce cell cycle arrest leading to senescence. All four groups of cells, with no drug treatment, with CPT treatment, with both CPT and CHX treatment, or with 10 Gy radiation treatment, were then incubated with our NIR-BG probe, followed by flow cytometry (FIGS. 16-19). Importantly, CPT or radiation treated cells had significantly higher fluorescence compared to the untreated control cells; the higher fluorescence presumably resulted from the expressed senescence-associated β-gal (SABG), which turned on the fluorescence of the NIR-BG probe. Meanwhile, the fluorescence in cells treated with both CPT and CHX was significantly reduced comparing to the CPT-treated group, suggesting the suppressed senescence due to CHX treatment. The same trend was observed for both HeLa and MCF7 cells (FIGS. 16-19).

Since SABG is localized in the lysosome, we then performed confocal microscopy of the normal and senescent HeLa or MCF7 cells (Not shown). Fluorescence from the NIR-BG probe (NIR-BG channel) in CPT or radiation treated cells was strikingly higher than that of the control cells without treatment. More importantly, the red fluorescence from our probe overlapped mainly with the lysosomes (LAMP-1 channel), suggesting the high probability that our probe was activated in lysosomes, where SABG was expressed. This was further confirmed by co-staining the cells with anti-β-gal antibody (0-gal channel); our probe signal in senescent cells, induced either by chemotherapeutics or by radiation, was well colocalized with both lysosome and β-gal. This feature was observed in both HeLa cell groups and MCF7 cell groups. These results further confirmed that the NIR-BG could image chemotherapy and radiation therapy induced senescence in different types of cancer cells. X-gal staining also verified the existence of SABG in cells after chemotherapy and radiation therapy.

Figure 22:
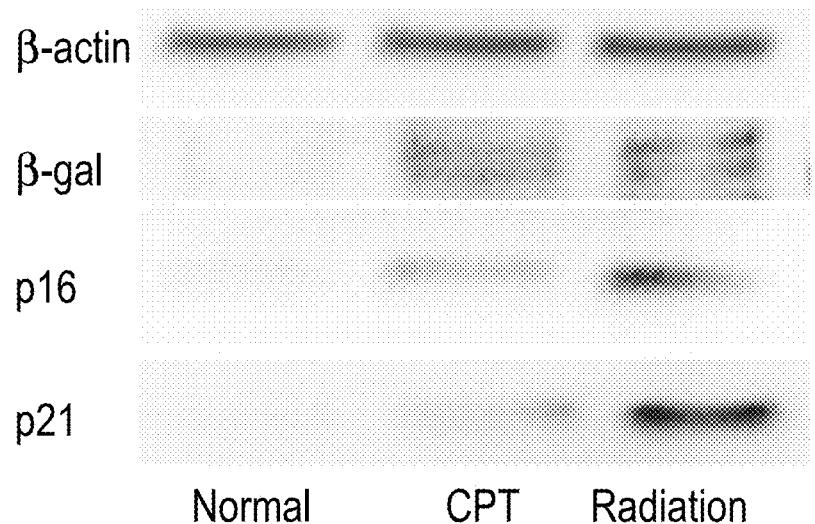
FIG. 22 is a western blot of β-gal, p16, and p21 expression in MCF7 cells without drug treatment, with CPT or radiation treatment. *P<0.001, P<0.005.
Figure 23:
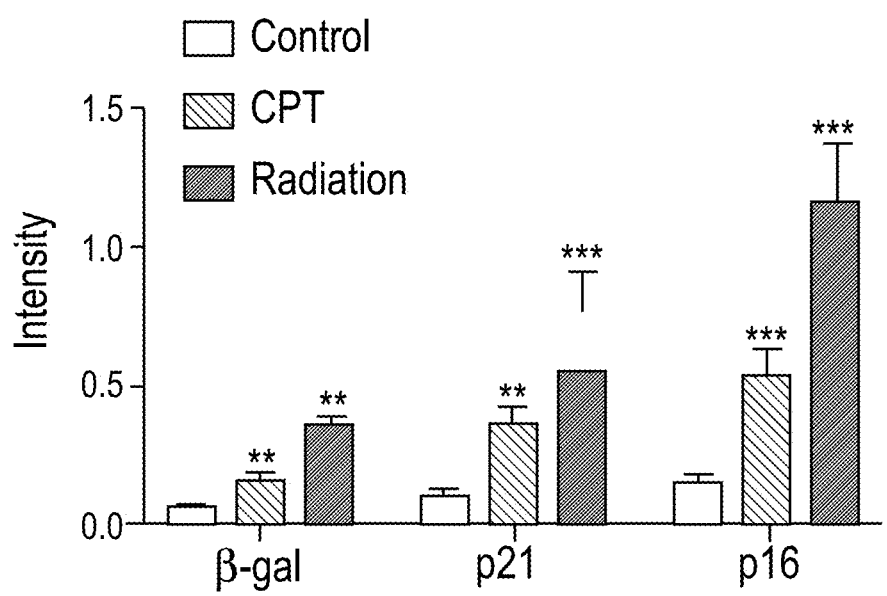
FIG. 23 is a quantification of FIG. 22.
Figure 24:
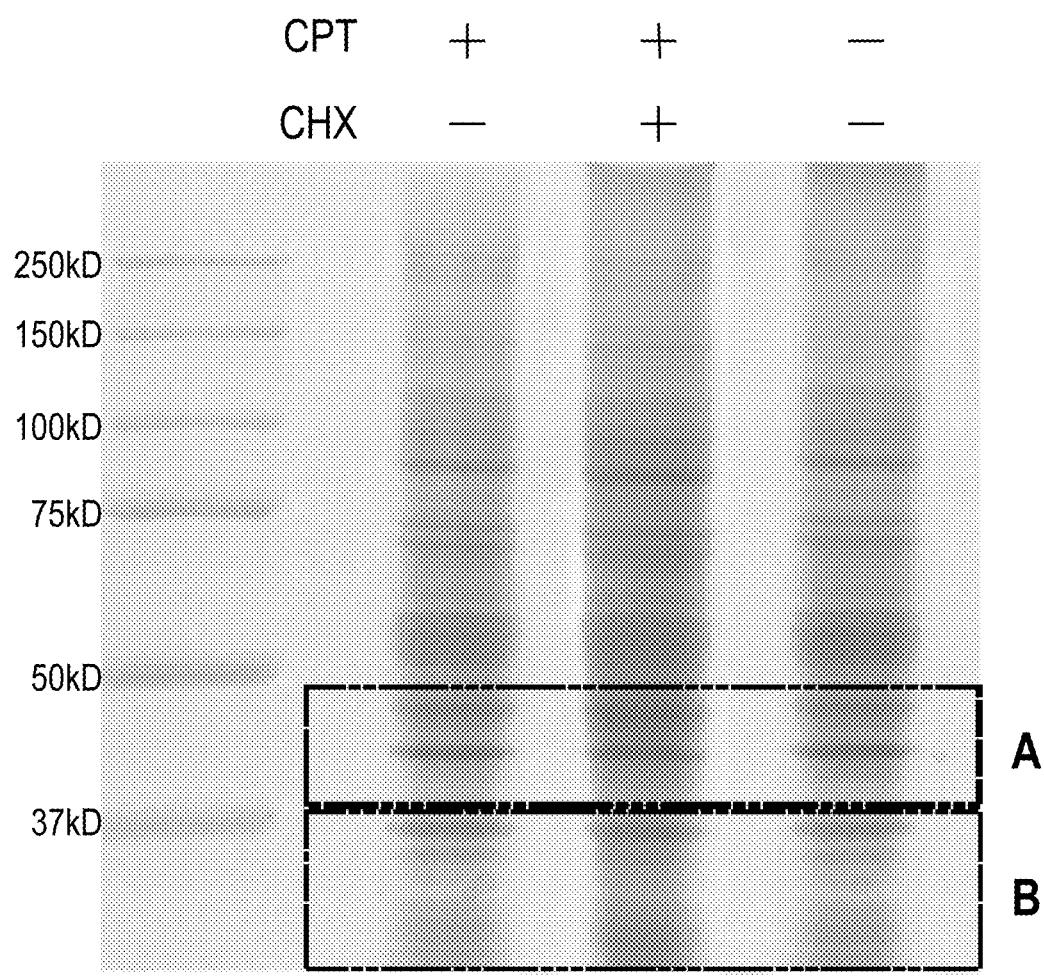
FIG. 24 is an SDS-PAGE of lysates of cells treated with CPT (left lane), CPT and CHX (middle lane), or without drug treatment (right lane). Sections A (beta-actin) and B (p16/p21) were used in Western blot analysis.

Cell cycle inhibitors p21 and p16 are often expressed by senescent cells[1]. Therefore, we examined the cell lysates of all cell samples from the imaging studies using Western blot (FIGS. 20-24). Western blot indicated that tumor suppressors p16 and p21 both increased in HeLa cells treated with CPT or radiation compared with normal HeLa cells (FIGS. 20, 21), confirming the cell samples we used were indeed senescent, and the induction of senescence by CPT or radiation was at least partially through p53 pathway, as p21 is typically induced directly by p53. In addition to HeLa cells, MCF7 cells also expressed higher levels of p16 and p21 upon CPT treatment (FIGS. 22, 23). The Western blot results confirmed the senescent state of these drug or radiation treated cells used in the imaging experiments. Interestingly, β-gal levels in drug or radiation treated HeLa or MCF7 cells were all elevated compared with the control cells, further suggesting the activation of β-gal enzymatic activity during senescence.

Example 3—Real-Time Imaging of Senescence in Tumor Models

Figure 25A:
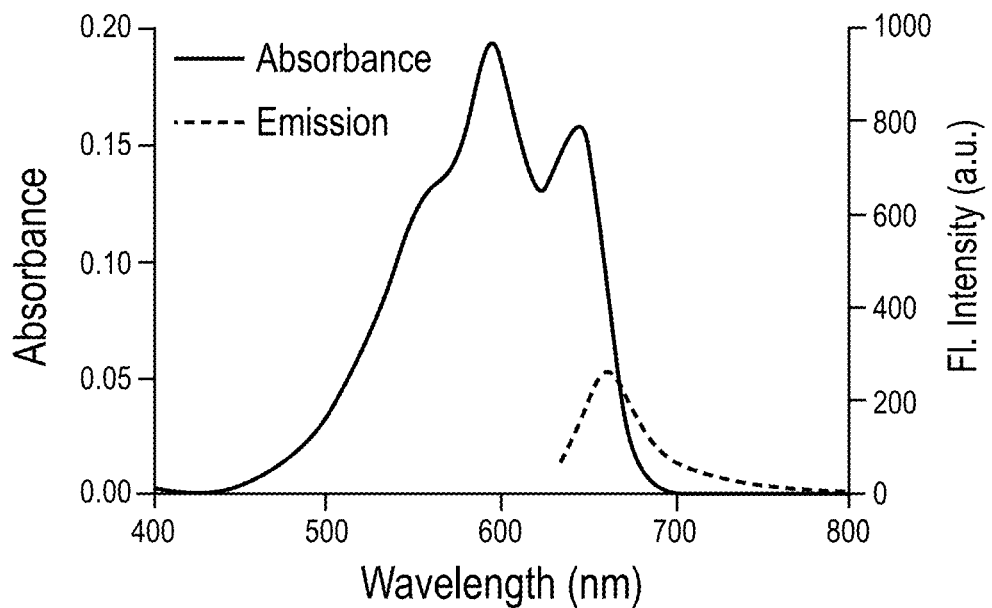
FIG. 25A is absorbance and emission spectra of the unactivated NIR-BG probe by β-galactosidase.
Figure 25B:
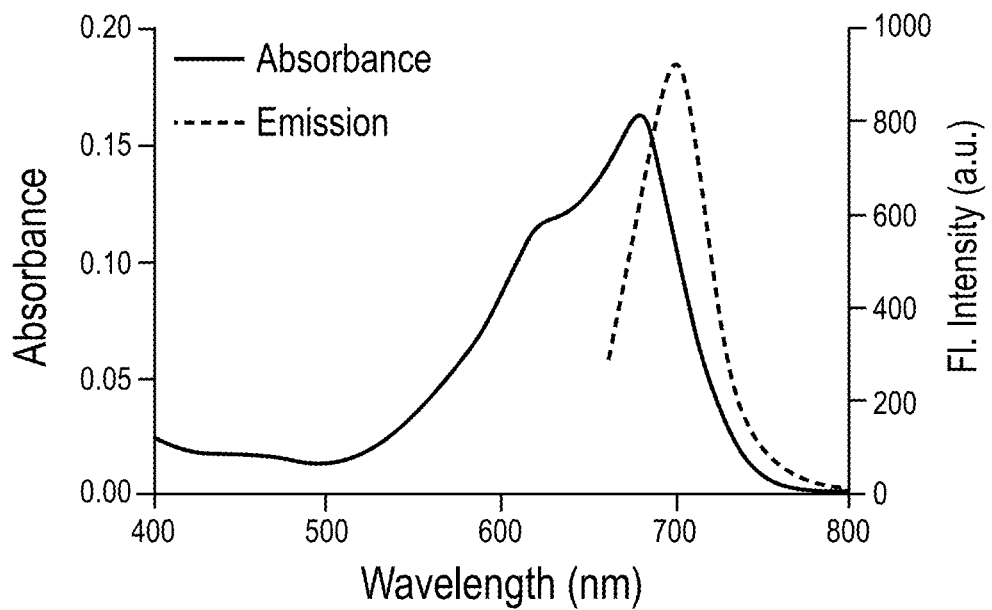
FIG. 25B is absorbance and emission spectra of the activated NIR-BG probe by β-galactosidase.

Successful detection of cellular senescence in vitro allowed us to further examine the capability of NIR-BG to visualize senescence in tumors in living mice. It is important to note that unactivated NIR-BG's absorption peaks around 640 nm and emission peaks around 660 nm, while the activated probe NIR-BG has the maximal absorption and emission at 680 nm and 710 nm respectively (FIGS. 25A, 25B). The imaging instrument IVIS spectrum can take advantage of this major difference between the unactivated and activated probe, therefore we examined our animals using two different filter settings (Ex640 nm/Em680 nm for unactivated probe and Ex675 nm/Em720 nm for the activated probe).

In a preliminary experiment, we used the genetically modified mice colon cancer cell line CT26 to determine whether NIR-BG could differentiate tumors with and without active β-gal (Not shown). The LacZ(+) CT26.CL25 tumors showed significantly higher signals of NIR-BG than CT26.WT tumors at 1 h after probe injection using 675 nm excitation and 720 nm emission filter setting; while their difference was minimal when using 640 nm excitation and 680 nm emission setting. This result suggested the unactivated form of NIR-BG could distribute to tumor with little influence by the β-gal expression, and the probe could be activated in β-gal expressing tumors therefore was detected upon 675 nm excitation and 720 nm emission. We also confirmed β-gal expression in resected whole tumor and tumor slides (Not shown). Immunofluorescent staining of the resected tumor tissues also showed homogenous distribution of probe NIR-BG which overlapped with β-gal in the CT26.CL25, but not in the CT26.WT tumors.

Figure 26:
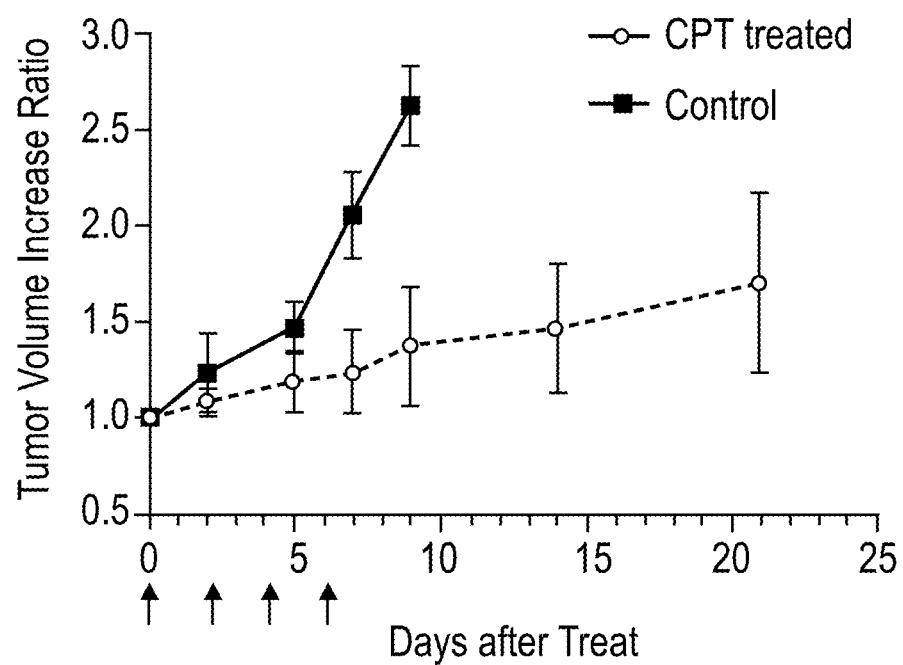
FIG. 26 is depicts the HeLa tumor growth curve with and without CPT treatment. The arrows below the x-axis indicate the CPT administration time. (The tumors of control group reached the maximum volume limitation and were imaged and euthanized.)
Figure 27:
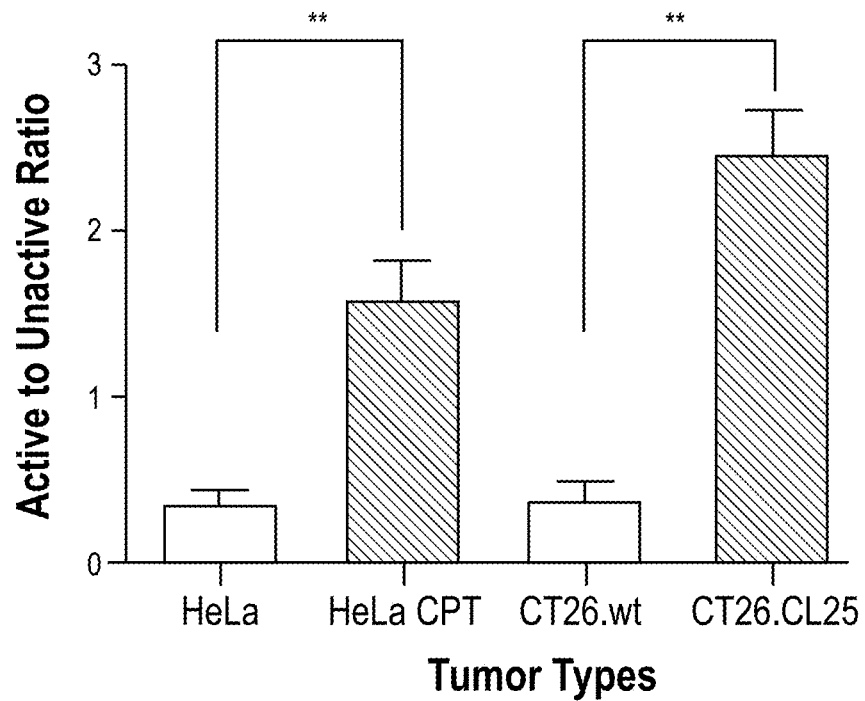
FIG. 27 is quantification of the probe activation as seen in fluorescence imaging of mice bearing CT26 HeLa tumors with or without CPT treatment.
Figure 28:
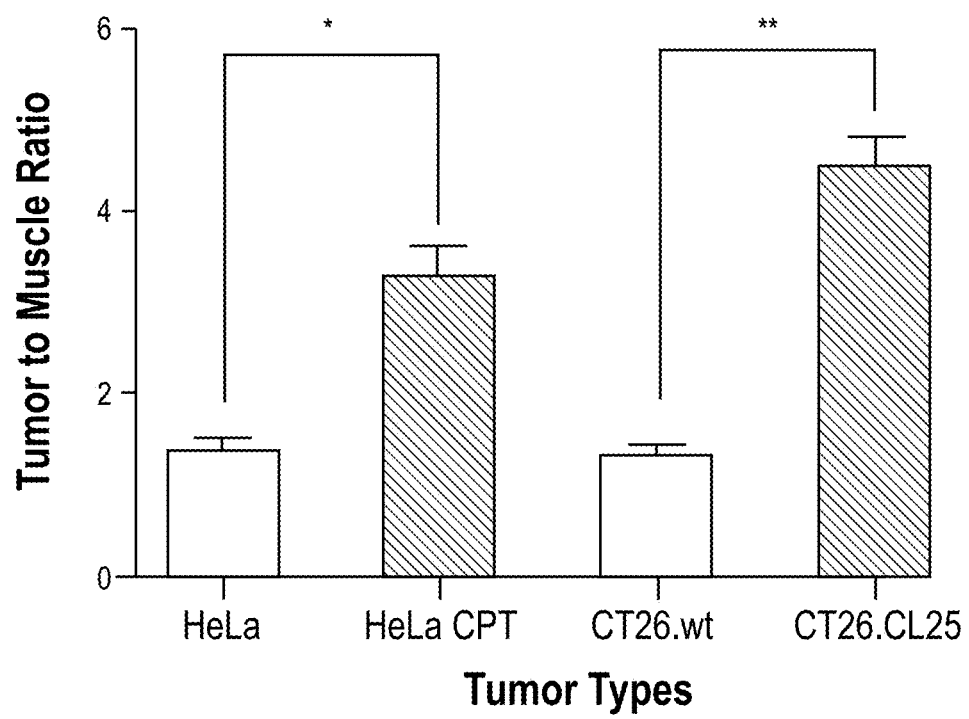
FIG. 28 is quantification of the probe activation of the tumor-to-muscle ratio as seen in fluorescence imaging of mice bearing CT26 HeLa tumors with or without CPT treatment.

We then moved on to HeLa xenografted mice models to see whether probe NIR-BG could visualize chemotherapy-induced senescence in tumors. (FIGS. 26-28) Tumor-bearing mice were first systemically treated with CPT or saline before the probe NIR-BG was injected. With the treatment of CPT, the tumor growth was significantly inhibited compared to the mice group receiving saline only (FIG. 26). We were delighted to find that NIR-BG behaved similarly in the drug-treated mice (with drug-induction triggered expression of β-gal) to the CT26 tumor models (with genetically expressed β-gal). HeLa tumors receiving either CPT treatment or saline showed similar signal of NIR-BG while using the 640 nm excitation and 680 nm emission filter setting, however, there was a significantly higher signal from the activated form of NIR-BG (observed using 675 nm excitation and 720 nm emission filter) in the HeLa tumors with CPT treatment. While not depicted, resected intact whole tumor staining, histochemical staining with X-gal and immunofluorescent staining of tumor tissue with antibodies against β-gal further confirmed the probe activation in senescent tumors.

Example 4—Detection of β-Gal in Senescent Cells by NIR-BG1 and NIR-BG2

To investigate the imaging ability and difference of NIR-BG2 and NIR-BG1 to detect (3-gal in senescent cells, HeLa cells were imaged after inducing senescence and compared with normal HeLa cells. Both NIR-BG2 and NIR-BG1 showed NIR signals in the senescent HeLa cells but the signal of NIR-BG2 was significantly higher than that from NIR-BG1 (Not shown). In addition to cellular uptake, the higher fluorescence in senescent cells was due to the attachment of activated NIR-BG2 to the β-gal and some other proteins. Meanwhile, no significant signal was observed in the normal HeLa cells.

In order to further verify that our probe can specifically detect β-gal in cells, CT26.CL25 cells were imaged with our probes and compared with the CT26.WT cells. The fluorescence microscope imaging showed that the CT26.CL25 had high NIR fluorescence from NIR-BG2 and NIR-BG1. The signal from the NIR-BG2 was significantly higher than that from NIR-BG1 while CT26.WT showed background signal in the NIR channel.

The dynamic clearance of probes by CT26.CL25 cells showed that the NIR-BG1 will be cleared out within 24 h while the NIR-BG2 could accumulate in the cells for more than 24 hours. These results support the contention that the NIR-BG2 is a self-immobilizing probe which is more specific and sensitive to detect the β-gal in senescent cells and would be used for in vivo imaging chemotherapy induced cancer senescence.

Example 5—In Vivo Visualization of Senescence by NIR-BG1 and NIR-BG2

HeLa xenografts imaging was successfully performed to further evaluate the capability of NIR-BG1 and NIR-BG2 to visualize senescence in vivo. HeLa tumor-bearing mice were treated with CPT or saline to induce the senescent cancer cells. After being injected NIR-BG1 or NIR-BG2 through tail vein injection, the CPT treated tumor showed significantly increased fluorescence compared to the saline treated tumor. The quantification of the optical imaging showed that the fluorescence from the senescent tumor was 3.06 (with NIR-BG2) and 2.84 (with NIR-BG1) times higher than normal tumor. Importantly, compared with NIR-BG1, the NIR-BG2 showed much higher signal and extended accumulation in the tumors which due to the attachment to the proteins after being activated. Ex vivo imaging and quantitative analysis of the tumors and organs further confirmed the in vivo imaging results.

Immunohistochemistry staining with X-gal confirmed the success of the chemotherapy induced senescence in the HeLa tumors. Moreover, fluorescence imaging of the slides further revealed the uptake of the probes in the senescent tumors which further certified the NIR-BG2 is better than NIR-BG1 for detecting senescent tumor cells in vivo.

What is claimed is:

1. A probe for visualization of senescent cells wherein the probe has the chemical structure:

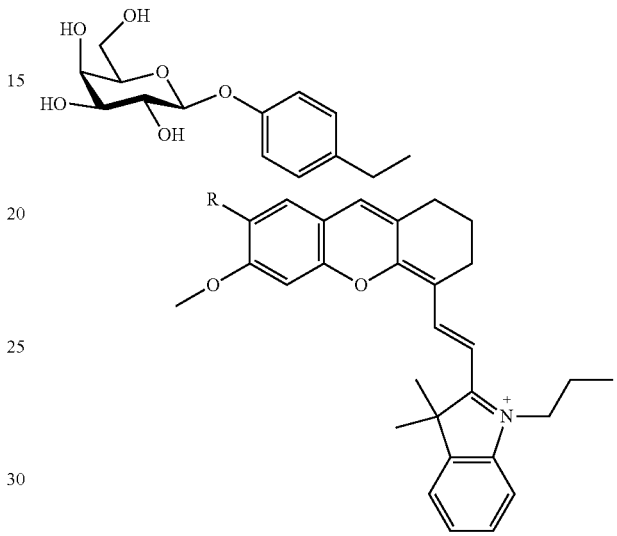

where R is $CHF_2$.

2. A method for detecting or visualizing cell senescence comprising delivering to one or more cells a senescence visualizing probe having the chemical structure:

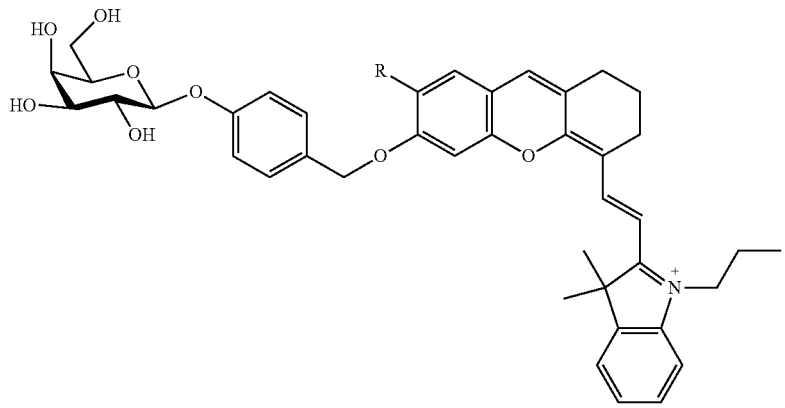

where R is $CHF_2$.

3. The method of claim 2 wherein the cells are in vivo.

* * * * *